United States Patent [19]

Cann et al.

[11] Patent Number: 5,172,695
[45] Date of Patent: Dec. 22, 1992

[54] METHOD FOR IMPROVED PREDICTION OF BONE FRACTURE RISK USING BONE MINERAL DENSITY IN STRUCTURAL ANALYSIS

[76] Inventors: Christopher E. Cann, 53 Carmel St., San Francisco, Calif. 94117; Kenneth G. Faulkner, 608 Lancaster Dr., Lafayette, Calif. 94549

[21] Appl. No.: 580,045

[22] Filed: Sep. 10, 1990

[51] Int. Cl.$^5$ .............................................. A61B 6/00
[52] U.S. Cl. .................................. 128/653.1; 378/54
[58] Field of Search ............... 128/653 R; 378/54–56, 378/88–90; 382/4, 6

[56] References Cited

U.S. PATENT DOCUMENTS

| | | | |
|---|---|---|---|
| 4,101,795 | 7/1978 | Fukumoto et al. | 128/662.03 |
| 4,811,373 | 3/1989 | Stein | 378/54 |
| 4,829,549 | 5/1989 | Vogel et al. | 128/653 |

FOREIGN PATENT DOCUMENTS 3726456 4/1988 Fed. Rep. of Germany ........ 378/54

OTHER PUBLICATIONS

Huiskes et al., "A Survey of Finite Element Analysis in Orthopedic Biomechanics: The First Decade", Journal Biomechanics vol. 16 No. 6 1983 pp. 385–409.

*Primary Examiner*—Ruth S. Smith
*Attorney, Agent, or Firm*—Townsend and Townsend

[57] ABSTRACT

A non-invasive in-vivo method of analyzing a bone for fracture risk includes obtaining data from the bone such as by computed tomography or projection imaging which data represents a measure of bone material characteristics such as bone mineral density. The distribution of the bone material characteristics is used to generate a finite element method (FEM) mesh from which load capability of the bone can be determined. In determining load capability, the bone is mathematically "compressed", and stress, strain force, force/area versus bone material characteristics are determined.

9 Claims, 4 Drawing Sheets

METHOD FOR IMPROVED PREDICTION OF BONE FRACTURE RISK USING BONE MINERAL DENSITY IN STRUCTURAL ANALYSIS

This invention was made with Government support under Grant No. 1 P01-DK-39964 awarded by the National Institute of Health and Subcontract 956084 awarded by NASA-JPL. The Government has certain rights in this invention

BACKGROUND OF THE INVENTION

This invention relates generally to the analysis of bone structure for determining risk of fracture, and more particularly the invention relates to an in vivo non-invasive method of determining bone fracture analysis by obtaining a measure of bone mineral density, establishing bone structure, and analyzing the structure for load carrying capability.

DESCRIPTION OF PRIOR ART

The amount of bone, or bone mineral density (BMD), or other properties of bone such as the speed of sound, are used conventionally to evaluate the skeletal status of individuals in an effort to predict the susceptibility of that bone, or by inference other bones in the patient, to fracture under minimal applied loads such as those encountered in normal daily living. This evaluation is done in the common use by passing a collimated beam of radiation through an object such as a person or inanimate object and measuring the transmitted photons on the opposite side of the object. The intensity of transmitted photons is compared to the intensity transmitted through a known object for the purpose of calibration. The calibrated intensity is used to describe some property of the object, such as bone mineral in the path of the beam. Alternatively, scattered or reflected radiation can be analyzed instead of transmitted radiation (such as Compton scattered photons or ultrasound). Many different types of apparatus can be used to do this, including but not limited to: computed tomography scanners, x-ray or radioisotope source projection imaging systems (including film), single-beam scanners or ultrasound devices. For all devices, the eventual outcome is a quantitative measurement of an average property of the bone measured.

Some devices generate an image of the object properties measure. Such images can be analyzed using various methods to give a regional distribution of the object properties, and these distributions are at times compared to distributions derived from population-averaged data or to data derived from prior studies of the same object. Such comparisons are done in a region-by-region or point-by-point basis but are not used to derive specifically the distribution of material properties. The values derived from such analyses are compared to a large, previously-derived database of values from other individual measurements, both from individuals with fractured bones (osteoporotics) and those without fracture (normals) to determine how well the value measured can classify a given patient as osteoporotic or normal. In some cases, combinations of measurements from different regions or different bones are used to try to improve this classification procedure. However, in virtually all cases the use of such measurements explains only 50–60% of the variance in the predictive capability for classification.

In order to try to improve this predictive capability, researchers have attempted to correct the measured bone mineral density by some parameter of geometry, such as cross-sectional area. Other investigators have developed analytic models of bones in an attempt to incorporate structure information into the analysis of bone strength. While these models can provide some additional information, they require that each bone be modeled directly, and thus they cannot be used in a practical setting. The best data regarding strength of bones comes from direct mechanical testing of bone. It is impossible to test bones directly in the living subject, with the exception of long bones such as the ulna or tibia where bending stiffness properties have been determined. No other researchers have proposed a general method for direct determination of the mechanical strength or failure properties of individual bones in individual subjects.

SUMMARY OF THE INVENTION

An object of this invention is to provide a method to measure non-invasively (in vivo) the strength of an individual bone in an individual patient. This measurement can then be used to determine whether or not the bone will fracture under specified loading conditions such as those normally seen in daily living. It can also be used to estimate fracture risks under abnormal loading conditions such as occur in falling, jumping or during athletic events or heavy training regimens.

The invention uses the distribution of physical properties of bone measured non-invasively in an individual and mathematical analysis of that distribution to predict the risk that a bone may fracture under applied loads. The use of such methods relates to the clinical disease of osteoporosis, or in general metabolic bone diseases, although by inference such methods can also be used to evaluate bones in any situation where the amount of bone may be compromised, such as bone metastases in cancer, multiple myeloma, or Paget's disease. In a primary application, 3-dimensional quantitative computed tomography data acquired using a conventional CT scanner are used to determine the distribution of bone mineral density, this distribution is used to define bone material properties, and the finite element method of analysis is used to determine structural properties of the whole or a part of the bone. Other applications include the use of any 2-D or 3-D noninvasive method to determine the distribution of bone material properties, such distribution measured in an individual then analyzed by the finite element method to predict structural properties.

In the general application, the invention relates to the use of non-invasive methods to determine material properties of an object followed by use of these properties as input to a finite element method (FEM) of analysis to determine failure modes. In some cases, the relationship between the measured property (e.g. density) and the actual property of the object input into the analysis (e.g. Young's Modulus) may require information acquired under other conditions.

The invention and objects and features thereof will be more readily apparent from the following detailed description and appended claims when taken with the drawings.

DETAILED DESCRIPTION OF ILLUSTRATIVE EMBODIMENTS

An advantage of the invention is its ability to use specific information obtained about the distribution of material properties in a bone in a patient to determine noninvasively the strength of that bone. This information is then used to predict risk of fracture under specified loading conditions. Specifically, the distribution of bone material properties determined non-invasively using one of a number of techniques (computed tomography, projection imaging, ultrasound, magnetic resonance) is used as input to a finite element analysis of structural strength, and other parameters such as loading conditions and boundary conditions are also included in the model as needed. Using mathematical methods contained in commercially-available or specially written computer programs, the model of a bone can be incrementally loaded until failure, and the yield strength determined. Alternatively, other mechanical properties can be measured this way. This invention is the first method to incorporate the distribution of bone material properties of any individual bone into an analysis of that object's mechanical characteristics. In order to practice this invention, it is required to measure the distribution of a parameter of bone, relate this parameter to material properties, generate a matrix containing geometrical and material properties of the object, and subject this matrix to defined loading conditions using the known finite element method of analysis to determine mechanical characteristics of the object as a whole.

Figure 1:
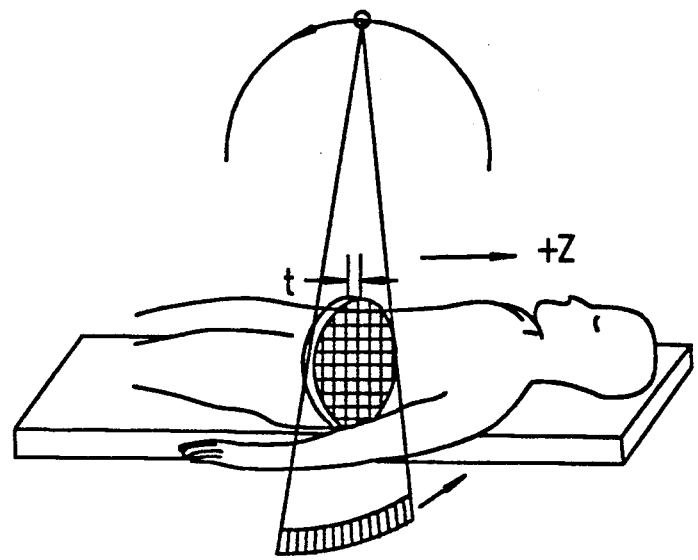
FIG. 1 is a schematic illustrating one apparatus to acquire data for the distribution of material properties in accordance with one embodiment of the invention.

A computed tomography (CT) imaging system as employed in accordance with one embodiment of the invention is illustrated in FIG. 1. A radiation source is mounted on a conventional gantry with a radiation detector on the opposing side of the patient. The CT imaging system is used to obtain an image of the patient within the reconstruction area, such image representing an x-y map of the x-ray attenuation properties of the patient and having a finite thickness in the z-axis defined as the "slice thickness". The CT scanner table is incremented by a preset amount, normally the slice thickness and a second image is obtained. The process is repeated until enough images have been obtained so that a whole bone or a desired part of a bone is included in the data set.

The output of the apparatus of FIG. 1 is conventionally a single number or several numbers representing an average material property of the bone. Our invention takes the data from such apparatus prior to the reduction to average properties, converts the data to a matrix of the geometrical distribution of material properties, uses the matrix as input to conventional finite element analysis software, and uses the finite element method (FEM) of analysis to generate mechanical properties. See for example Huiskes "A Survey of Finite Element Analysis in Orthopedic Biomechanics: The First Decade," Pergamon Press Ltd., 1983 pages 385-409. Such properties are output from the finite element analysis directly or by analysis of preliminary output such as a stress vs. strain curve. A property such as the yield stress of the bone is then used to characterize the patient's risk of fracturing the bone, or by inference, of fracturing other, similar, bones. The CT scanner is calibrated so that the x-ray attenuation properties can be related to properties of the bone, such as bone mineral density. Individual regions of bone mineral density can be measured from this data set (Cann CE, Genant HK: "Precise measurement of vertebral mineral content using computed tomography," J. Comput. Assist. Tomogr. 4:493-500, 1980).

Figure 2:
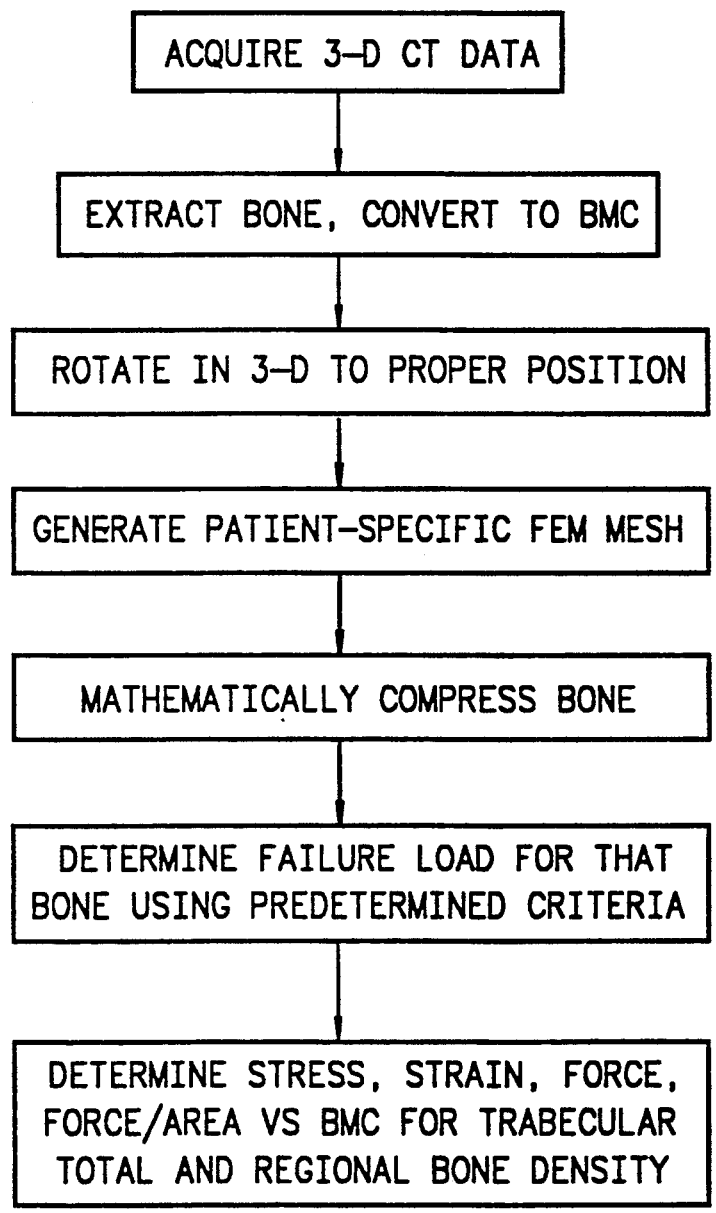
FIG. 2 illustrates one method of practicing the invention.
Figure 3A:
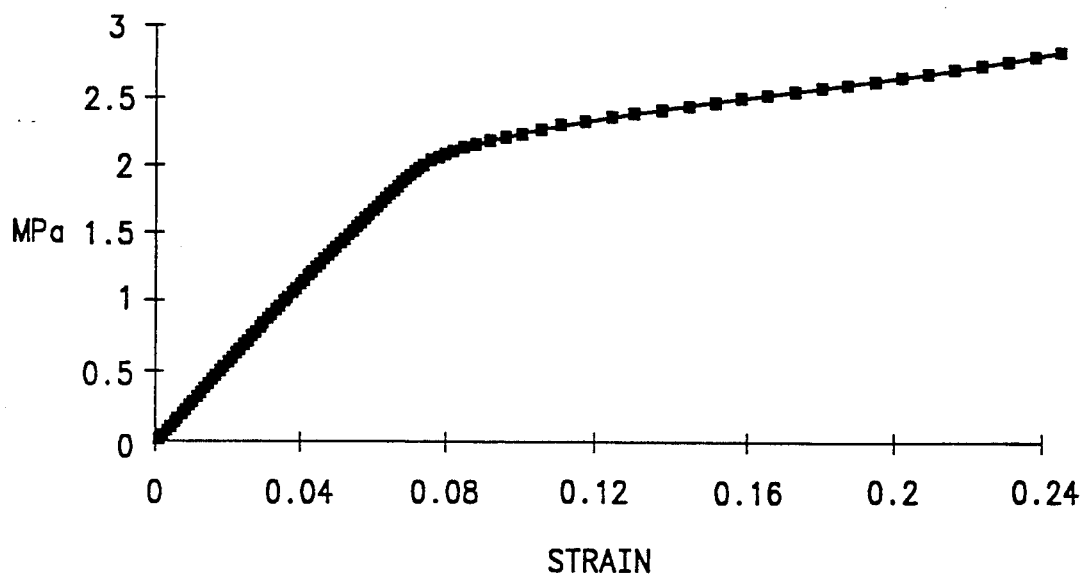
FIG. 3A and 3B illustrate one means of obtaining bone fracture determination using the invention.
Figure 3B:
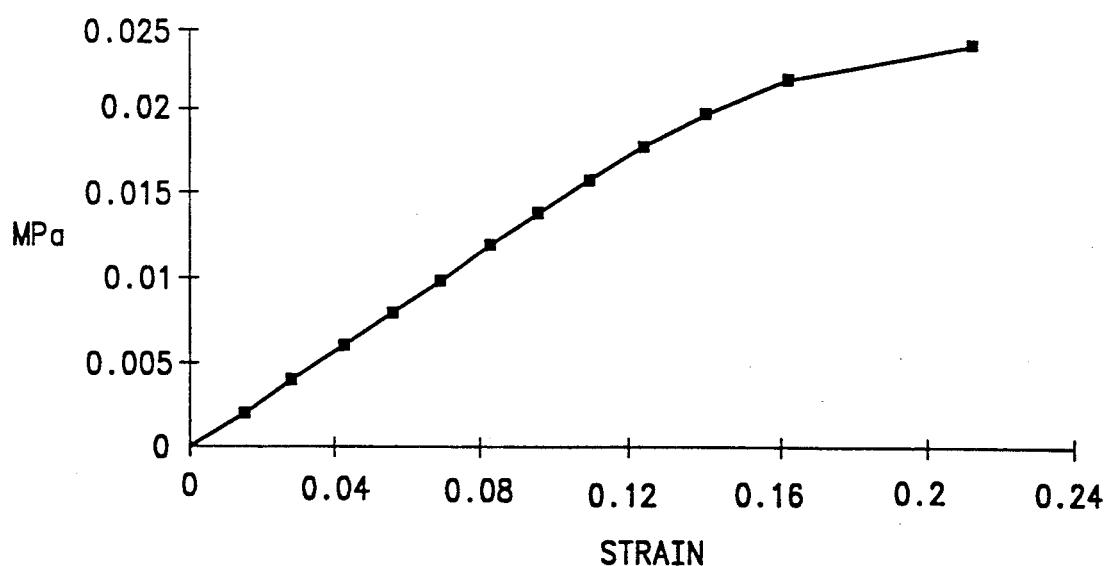

In FIG. 2, the 3-D CT data set is acquired and the information about the distribution of bone is preserved. The original CT data are then processed using known methods to convert each point in the distribution to bone material characteristics (BMC), and the bone can be separated from surrounding materials not used in the analysis, if desired. The bone data set is rotated in 3 dimensions to an orientation required for the mathematical loading analysis. The coordinates of each distribution CT point and their material properties are used to generate a conductivity matrix or mesh describing the exact relationships among the regions of the bone. The mesh is input to finite element method (FEM) analysis software using appropriate boundary conditions. FEM models have heretofore been used in orthopedic biomechanics to model bones for use in designing orthopedic prostheses. The bone is mathematically "compressed" for structure analysis. Force versus displacement (stress vs. strain) information about the elements in the mesh (that is, the regions of the bone) is determined and such information can be plotted on a graph, for example in FIG. 3, or analyzed on the computer to determine the yield strength of the bone (the point at which elastic deformation converts to plastic deformation). In FIG. 3A stress vs. strain in normal bone is plotted, and in FIG. 3B stress vs. strain in osteoporotic bone is plotted.

Figure 4A:
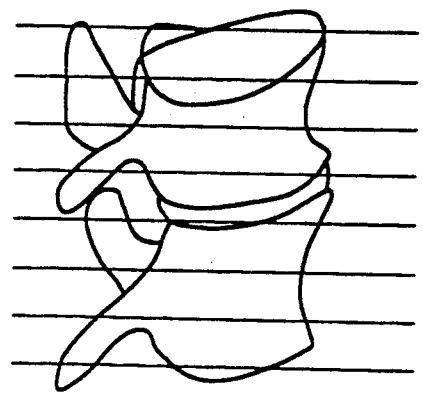
FIGS. 4A-4C illustrate the mathematical analysis of a vertebra in accordance with the invention.
Figures 4B, 4C:
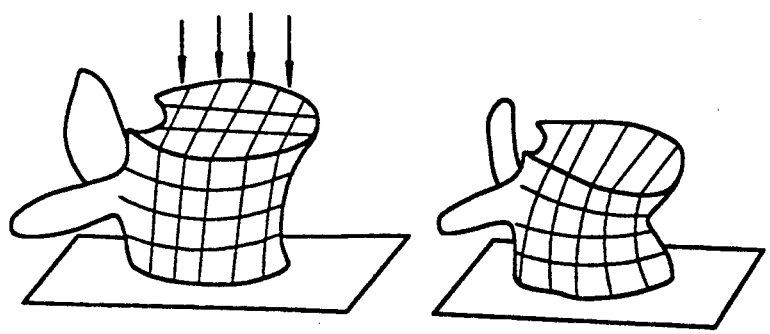

This is further illustrated in FIGS. 4A, 4B, and 4C. FIG. 4A illustrates the original scan plane orientation for CT scans of vertebrae. The bone material characteristics of a vertebra of interest are determined and rotated in orientation for uniform loading as shown in FIG. 4B. The elements of the rotated vertebra after the mathematical compression test are illustrated in FIG. 4C.

Figure 5:
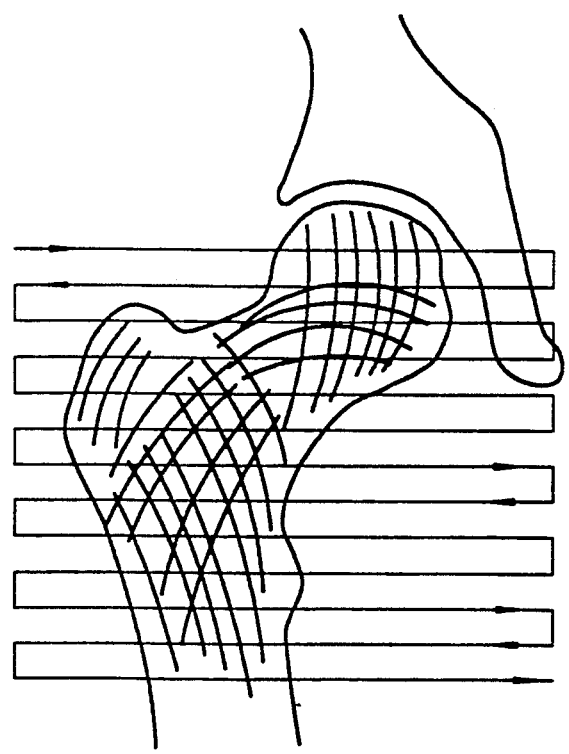
FIG. 5 is a schematic illustrating another apparatus for acquiring data for the distribution of material properties in accordance with another embodiment of the invention.

FIG. 5 illustrates analysis of a hip bone (proximal femur) using a two dimensional projection raster scan in accordance with another embodiment of the invention. Again, the scan data for the bone is extracted and converted to bone material characteristics (e.g. bone mineral density). Other known techniques can be used for obtaining the initial data representing the bone characteristics including DPA, DEXA, and QDR.

There has been described an improved method of prediction of bone fracture risk by obtaining data from which distributed bone material characteristics such as bone mineral density can be determined and from which structural analysis can be made. The method is especially useful in diagnosis and treatment of patients with or predisposed to osteoporosis, but the method can be used for other individuals such as athletes and astronauts in training. Further, the FEM model can be modified to reflect aging of an individual.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A method of determining fracture risk of a bone in vivo under normal loading conditions based on the density and geometric distribution of bone mineral comprising the steps of non-invasively obtaining x-ray attenuation data from said bone representing a measure of bone mineral, converting said data into a bone mineral distribution characteristic, generating a finite element method model based on said bone mineral distribution characteristic, and determining load capability of said bone using said FEM model.

2. The method as defined by claim 1 wherein said step of non-invasively obtaining x-ray attenuation data includes acquiring computed tomography (CT) data for said bone.

3. The method as defined by claim 1 wherein said step of non-invasively obtaining x-ray attenuation data includes obtaining projection image data.

4. The method as defined by claim 2 wherein said step of obtaining x-ray attenuation projection image data includes a raster scan of a particle beam through said bone.

5. The method as defined by claim 1 wherein said step of determining load capability of said bone includes mathematically compressing said FEM model.

6. The method as defined by claim 5 wherein said step of determining load capability further includes determining stress and strain versus bone material characteristics for said bone.

7. The method as defined by claim 6 wherein said step of determining load capability further includes determining failure load for said bone.

8. The method as defined by claim 7 and further including the step of altering said FEM model to represent aging of said bone.

9. The method as defined by claim 1 and further including the step of altering said FEM model to represent aging of said bone.

* * * * *